US007612163B1

(12) United States Patent
Liu et al.

(10) Patent No.: US 7,612,163 B1
(45) Date of Patent: Nov. 3, 2009

(54) PROKINETICIN 2β PEPTIDE AND ITS USE

(75) Inventors: Changlu Liu, San Diego, CA (US); Jingcai Chen, Beijing (CN)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 10/594,832

(22) PCT Filed: Mar. 29, 2005

(86) PCT No.: PCT/US2005/010279

§ 371 (c)(1),
(2), (4) Date: Jul. 16, 2007

(87) PCT Pub. No.: WO2005/097826

PCT Pub. Date: Oct. 20, 2005

Related U.S. Application Data

(60) Provisional application No. 60/557,733, filed on Mar. 29, 2004.

(51) Int. Cl.
C07K 1/00 (2006.01)
A61K 38/17 (2006.01)

(52) U.S. Cl. .......................... 530/324; 530/350; 514/2; 514/12

(58) Field of Classification Search .................. 530/324, 530/350; 514/2, 12
See application file for complete search history.

(56) References Cited

U.S. PATENT DOCUMENTS

2003/0059856 A1* 3/2003 Ames et al. ................. 435/7.21
2003/0092623 A1* 5/2003 Ferrara et al. ................. 514/12
2003/0235535 A1* 12/2003 Zhou et al. ................... 424/9.2

OTHER PUBLICATIONS

Achem et al., "A prokinetic approach to treatment of gastroesophageal reflux disease", *Dig Dis.*, 1998, 16:38-46.
Arad et al., "The fetal inflammatory response syndrome and associated infant morbidity", *IMAJ*, 2004, 6:766-769.
Briejer et al, "Idiopathic constipation: too few stools and too little knowledge", *Trends Pharmacol. Sci.*, 1999, 20:1-3.
Bullock et al., "Structural determinants required for the bioactivities of prokineticins and identification of prokinectin receptor antagonists", *Mol Pharmacology*, 2004, 65(3):582-588.
Chabre et al., "Coupling of the alpha 2A-adrenergic receptor to multiple G-proteins. A simple approach for estimating receptor-G-protein coupling efficiency in a transient expression system", *J Biol Chem.*, 1994, 269(8):5730-5734.
Cheng et al., "Prokineticin 2 transmits the behavioural circadian rhythm of the suprachiasmatic nucleus", *Nature*, 2002, 417:405-410.
Conklin et al., "Substitution of three amino acids switches receptor specificity of Gq alpha to that of Gi alpha", *Nature*, 1993, 363:274-276.
Efthimiou et al, "Role of biological agents in immune-mediated inflammatory diseases", *South Med J.*, 2005, 98(2): 192-204.

Ferrara et al., "Differential expression of the angiogenic factor genes vascular endothelial growth factor (VEGF) and endocrine gland-derived VEGF in normal and polycystic human ovaries", *Am. J. Pathol.*, 2003,162(6):1881-1893.
Hachem et al., "Bronchiolitis obliterans syndrome: pathogenesis and management", *Semin Thorac Cardiovasc Surg.*, 2004, 16(4):350-355.
Hickey et al., "Clinical implications of disturbances of uterine vascular morphology and function", *Baillieres Clin Obstet Gynaecol.*, 2000, 14(6):937-951.
Kisliouk et al., "Presence and regulation of endocrine gland vascular endothelial growth factor/prokineticin-1 and its receptors in ovarian cells", *J Clin Endocrinol Metab.*, 2003, 88(8):3700-3707.
LeCouter et al., "Identification of an angiogenic mitogen selective for endocrine gland endothelium",*Nature*, 2001, 412:877-884.
LeCouter et al., "Endocrine gland-derived VEGF and the emerging hypothesis of organ-specific regulation of angiogenesis", *Nat Med.*, 2002, 8(9):913-917.
LeCouter et al., "The role of EG-VEGF in the regulation of angiogenesis in endocrine glands", *Cold Spring Harb Symp Quant Biol.*, 2002, 67:217-221.
LeCouter et al., "The endocrine-gland-derived VEGF homologue Bv8 promotes angiogenesis in the testis: Localization of Bv8 receptors to endothelial cells", *Proc Natl Acad Sci USA*, 2003, 100(5):2685-2690.
LeCouter et al., "Mouse endocrine gland-derived vascular endothelial growth factor: a distinct expression pattern from its human ortholog suggests different roles as a regulator of organ-specific angiogenesis", *Endocrinology*, 2003, 144(6):2606-2616.
Li et al., "Identification of two prokineticin cDNAs: Recombinant proteins potently contract gastrointestinal smooth muscle", *Mol Pharmacol*, 2001, 59(4):692-698.
Lin et al., "Identification and molecular characterization of two closely related G protein-coupled receptors activated by prokineticins/endocrine gland vascular endothelial growth factor",*J Biol Chem.*, 2002, 277(22):19276-19280.
Lin et al., "Characterization of endocrine gland-derived vascular endothelial growth factor signaling in adrenal cortex capillary endothelial cells", *J Biol Chem.*, 2002, 277(10):8724-8729.
Liu et al., "Cloning and pharmacological characterizaiton of a fourth histamine receptor (H4) expressed in bone marrow", *Mol Pharmacol.*, 2001, 59(3):420-426.
Liu et al., "Comparison of human, mouse, rat and guinea pig histamine H4 receptors reveals substantial pharmacological species variation", *J Pharmacol Exp Ther.*, 2001, 299(1):121-130.
Liu et al., "Involvement of both Gq/11 and Gs proteins in gonadotropin-releasing hormone receptor-mediated signaling in LβT2 cells", *J Biol Chem.*, 2002, 277(35):32099-32108.
Masuda et al., "Isolation and identification of EG-VEGF/prokineticins as cognate ligands for two orphan G-protein-coupled receptors", *Biochem Biophys Res Commun.*, 2002, 293:396-402.
Medford et al., "Vascular endothelial growth factor gene polymorphism and acute respiratory distress syndrome", *Thorax*, 2005, 60:244-248.

(Continued)

*Primary Examiner*—Jon P Weber
*Assistant Examiner*—Abdel A Mohamed

(57) ABSTRACT

A PK2β peptide is described, which, as an agonist of prokineticin receptor 1, is useful for treating lung and gastrointestinal diseases or disorders mediated by PKR1 activity.

3 Claims, 8 Drawing Sheets

OTHER PUBLICATIONS

Mollay et al. "Bv8, a small protein from frog skin and its homologue from snake venom induce hyperalgesia in rats", *Eur J Pharmacol.*, 1999, 374:189-196.

Nakayama, "Furin: a mammalian subtilisin/kex2p-like endoprotease involved in processing of a wide variety of precursor proteins", *Biochem J.*, 1997, 327:625-635.

Negri et al., "Nociceptive sensitization by the secretory protein Bv8," *Br J Pharmacol.*, 2002, 137(8):1147-1154.

Samsom et al., "Abnormal gastric and small intestinal motor function in diabetes mellitus", *Dig Dis.*, 1997, 15:263-274.

Schweitz et al., "Purification and pharmacological characterization of peptide toxins from the black mamba (*Dendroaspis polylepis*) venom", *Toxicon*, 1990, 28(7):847-856.

Schweitz et al., "MIT(1), a black mamba toxin with a new and highly potent activity on intestinal contraction", *FEBS Lett.*, 1999, 461:183-188.

Soga et al., "Molecular cloning and characterization of prokineticin receptors," *Biochim. Biophys. Acta.*, 2002, 1579:173-179.

Steiner et al., "The new enzymology of precursor processing endoproteases", *J Biol Chem.*, 1992, 267(33):23435-23438.

Tonini, "Recent advances in the pharmacology of gastrointestinal prokinetics", *Pharmacol Res.*, 1996, 33(4-5):217-226.

Wechselberger et al., "The mammalian homologues of frog Bv8 are mainly expressed in spermatocytes", *FEBS Lett.*, 1999, 462:177-181.

Weissgerber et al., "The role of regular physical activity in preeclampsia prevention", *Med. Sci. Sports Exerc.*, 2004, 2024-2031.

Yanagita et al., "Processing of mutated proinsulin with tetrabasic cleavage sites to mature insulin reflects the expression of furin in nonendocrine cell lines", *Endocrinology*, 1993, 133(2): 639-644.

Zhang et al., "Expression of endocrine gland-derived vascular endothelial growth factor in ovarian carcinoma", *Clin Cancer Res.*, 2003, 9:264-272.

\* cited by examiner

SEQUENCE LISTING

<160> NUMBER OF SEQ ID NOS: 29

<210> SEQ ID NO 1
<211> LENGTH: 56
<212> TYPE: PRT
<213> ORGANISM: Homo sapiens

<400> SEQUENCE: 1

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

Pro Met Gly Lys Leu Gly Asp Ser Cys His Pro Leu Thr Arg Lys Asn
        35                  40                  45

Asn Phe Gly Asn Gly Arg Gln Glu
    50                  55

<210> SEQ ID NO 2
<211> LENGTH: 56
<212> TYPE: PRT
<213> ORGANISM: mouse

<400> SEQUENCE: 2

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

```
Pro Met Gly Gln Val Gly Asp Ser Cys His Pro Leu Thr Arg Lys Ser
         35                  40                  45
His Val Ala Asn Gly Arg Gln Glu
    50                  55

<210> SEQ ID NO 3
<211> LENGTH: 40
<212> TYPE: DNA
<213> ORGANISM: Artificial
<220> FEATURE:
<223> OTHER INFORMATION: PKR1 primer P1

<400> SEQUENCE: 3
acgtgaattc gccaccatgg agaccaccat ggggttcatg                         40

<210> SEQ ID NO 4
<211> LENGTH: 40
<212> TYPE: DNA
<213> ORGANISM: Artificial
<220> FEATURE:
<223> OTHER INFORMATION: PKR1 primer P2

<400> SEQUENCE: 4
acgtagcggc cgcttatttt agtctgatgc agtccacctc                         40

<210> SEQ ID NO 5
<211> LENGTH: 39
<212> TYPE: DNA
<213> ORGANISM: Artificial
<220> FEATURE:
<223> OTHER INFORMATION: PKR2 primer P3

<400> SEQUENCE: 5
acgcgaattc gccaccatgg cagcccagaa tggaaacac                          39

<210> SEQ ID NO 6
<211> LENGTH: 39
<212> TYPE: DNA
<213> ORGANISM: Artificial
<220> FEATURE:
<223> OTHER INFORMATION: PKR2 primer P4

<400> SEQUENCE: 6
acgcatgcgg ccgcgtcact tcagcctgat acagtccac                          39

<210> SEQ ID NO 7
<211> LENGTH: 59
<212> TYPE: DNA
<213> ORGANISM: Artificial
<220> FEATURE:
<223> OTHER INFORMATION: Human PK1 primer P5

<400> SEQUENCE: 7
tcatcacgaa ttcgatgacg acgataaggc tgtgatcaca ggggcctgtg agcgggatg    59

<210> SEQ ID NO 8
<211> LENGTH: 40
<212> TYPE: DNA
<213> ORGANISM: Artificial
<220> FEATURE:
<223> OTHER INFORMATION: Human PK1 primer P6

<400> SEQUENCE: 8
acgataggat ccctaaaaat tgatgttctt caagtccatg                         40
```

<210> SEQ ID NO 9
<211> LENGTH: 54
<212> TYPE: DNA
<213> ORGANISM: Artificial
<220> FEATURE:
<223> OTHER INFORMATION: Human PK2 primer P7

<400> SEQUENCE: 9
catcacgaat tcgatgacga cgataaggcc gtgatcaccg ggcttgtga caag       54

<210> SEQ ID NO 10
<211> LENGTH: 39
<212> TYPE: DNA
<213> ORGANISM: Artificial
<220> FEATURE:
<223> OTHER INFORMATION: Human PK2 primer P8

<400> SEQUENCE: 10
acgataggat ccttactttt gggctaaaca aataaatcg                      39

<210> SEQ ID NO 11
<211> LENGTH: 39
<212> TYPE: DNA
<213> ORGANISM: Artificial
<220> FEATURE:
<223> OTHER INFORMATION: Human PK2-f primer P9

<400> SEQUENCE: 11
atcgagaatt cgccaccatg aggagcctgt gctgcgccc                      39

<210> SEQ ID NO 12
<211> LENGTH: 48
<212> TYPE: DNA
<213> ORGANISM: Artificial
<220> FEATURE:
<223> OTHER INFORMATION: Human PK2-f primer P10

<400> SEQUENCE: 12
ggatccctac ttatcgtcgt catccttata atccttttgg gctaaaca            48

<210> SEQ ID NO 13
<211> LENGTH: 42
<212> TYPE: DNA
<213> ORGANISM: Artificial
<220> FEATURE:
<223> OTHER INFORMATION: Human PK1 primer P11

<400> SEQUENCE: 13
acgtaagaat tcgccaccat gagaggtgcc acgcgagtct ca                  42

<210> SEQ ID NO 14
<211> LENGTH: 42
<212> TYPE: DNA
<213> ORGANISM: Artificial
<220> FEATURE:
<223> OTHER INFORMATION: Human PK1 primer P12

<400> SEQUENCE: 14
acgtaagaat tcctaaaaat tgatgttctt caagtccatg ga                  42

<210> SEQ ID NO 15
<211> LENGTH: 35
<212> TYPE: DNA
<213> ORGANISM: Artificial
<220> FEATURE:
<223> OTHER INFORMATION: Human PKR1 primer13

```
<400> SEQUENCE: 15
caacttcagc tacagcgact atgatatgcc tttgg                    35

<210> SEQ ID NO 16
<211> LENGTH: 35
<212> TYPE: DNA
<213> ORGANISM: Artificial
<220> FEATURE:
<223> OTHER INFORMATION: Human PKR1 primer P14

<400> SEQUENCE: 16
gacgaggacc gtctcggtgg tgaagtaggc ggaag                    35

<210> SEQ ID NO 17
<211> LENGTH: 35
<212> TYPE: DNA
<213> ORGANISM: Artificial
<220> FEATURE:
<223> OTHER INFORMATION: Human PKR2 primer P15

<400> SEQUENCE: 17
tctcctttaa cttcagttat ggtgattatg acctc                    35

<210> SEQ ID NO 18
<211> LENGTH: 35
<212> TYPE: DNA
<213> ORGANISM: Artificial
<220> FEATURE:
<223> OTHER INFORMATION: Human PKR2 primer 17

<400> SEQUENCE: 18
cgatgggatg gcaatgagaa tggacaccat ccaga                    35

<210> SEQ ID NO 19
<211> LENGTH: 39
<212> TYPE: DNA
<213> ORGANISM: Artificial
<220> FEATURE:
<223> OTHER INFORMATION: Human PK1 probe oligo

<400> SEQUENCE: 19
acctgtcctt gcttgcccaa cctgctgtgc tccaggttc                39

<210> SEQ ID NO 20
<211> LENGTH: 39
<212> TYPE: DNA
<213> ORGANISM: Artificial
<220> FEATURE:
<223> OTHER INFORMATION: PK2 and PK2beta probe oligo

<400> SEQUENCE: 20
tgggcaaact gggagacagc tgccatccac tgactcgta                39

<210> SEQ ID NO 21
<211> LENGTH: 43
<212> TYPE: DNA
<213> ORGANISM: Artificial
<220> FEATURE:
<223> OTHER INFORMATION: Human PKR1 probe oligo

<400> SEQUENCE: 21
ctgattgcct tggtgtggac ggtgtccatc ctgatcgcca tcc           43
```

<210> SEQ ID NO 22
<211> LENGTH: 40
<212> TYPE: DNA
<213> ORGANISM: Artificial
<220> FEATURE:
<223> OTHER INFORMATION: Human PKR2 probe oligo

<400> SEQUENCE: 22
cggatgaatt atcaaacggc tccttcctg atcgccttgg           40

<210> SEQ ID NO 23
<211> LENGTH: 33
<212> TYPE: DNA
<213> ORGANISM: Artificial
<220> FEATURE:
<223> OTHER INFORMATION: Human Beta-actin probe oligo

<400> SEQUENCE: 23
gagaagagct acgagctgcc tgacggccag gtc                33

<210> SEQ ID NO 24
<211> LENGTH: 34
<212> TYPE: DNA
<213> ORGANISM: Artificial
<220> FEATURE:
<223> OTHER INFORMATION: Human Beta-actin probe oligo 2

<400> SEQUENCE: 24
aagggtgtaa cgcaactaag tcatagtccg ccta                34

<210> SEQ ID NO 25
<211> LENGTH: 4
<212> TYPE: PRT
<213> ORGANISM: Artificial Sequence
<220> FEATURE:
<223> OTHER INFORMATION: Furin cleavage site

<400> SEQUENCE: 25

Arg Arg Lys Arg
1

<210> SEQ ID NO 26
<211> LENGTH: 4
<212> TYPE: PRT
<213> ORGANISM: Artificial Sequence
<220> FEATURE:
<223> OTHER INFORMATION: Furin cleavage site

<400> SEQUENCE: 26

Arg Ser Lys Arg
1

<210> SEQ ID NO 27
<211> LENGTH: 81
<212> TYPE: PRT
<213> ORGANISM: Homo Sapiens

<400> SEQUENCE: 27

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

Pro Met Gly Lys Leu Gly Asp Ser Cys His Pro Leu Thr Arg Lys Val
        35                  40                  45

```
Pro Phe Phe Gly Arg Arg Met His His Thr Cys Pro Cys Leu Pro Gly
    50                  55                  60
Leu Ala Cys Leu Arg Thr Ser Phe Asn Arg Phe Ile Cys Leu Ala Gln
65                  70                  75                  80
Lys

<210> SEQ ID NO 28
<211> LENGTH: 102
<212> TYPE: PRT
<213> ORGANISM: Homo Sapiens

<400> SEQUENCE: 28

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
                20                  25                  30

Pro Met Gly Lys Leu Gly Asp Ser Cys His Pro Leu Thr Arg Lys Asn
            35                  40                  45

Asn Phe Gly Asn Gly Arg Gln Glu Arg Arg Lys Arg Lys Arg Ser Lys
    50                  55                  60

Arg Lys Lys Glu Val Pro Phe Phe Gly Arg Arg Met His His Thr Cys
65                  70                  75                  80

Pro Cys Leu Pro Gly Leu Ala Cys Leu Arg Thr Ser Phe Asn Arg Phe
                85                  90                  95

Ile Cys Leu Ala Gln Lys
            100

<210> SEQ ID NO 29
<211> LENGTH: 102
<212> TYPE: PRT
<213> ORGANISM: mouse

<400> SEQUENCE: 29

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
                20                  25                  30

Pro Met Gly Gln Val Gly Asp Ser Cys His Pro Leu Thr Arg Lys Ser
            35                  40                  45

His Val Ala Asn Gly Arg Gln Glu Arg Arg Ala Lys Arg Arg Lys
    50                  55                  60

Arg Lys Lys Glu Val Pro Phe Trp Gly Arg Arg Met His His Thr Cys
65                  70                  75                  80

Pro Cys Leu Pro Gly Leu Ala Cys Leu Arg Thr Ser Phe Asn Arg Phe
                85                  90                  95

Ile Cys Leu Ala Arg Lys
            100
```

PROKINETICIN 2β PEPTIDE AND ITS USE

CROSS-REFERENCE TO RELATED APPLICATION

This application, which is a national phase under 35 U.S.C. 371 of International Application No. PCT/US2005/10279 filed Mar. 29, 2005, claims the benefit of priority to U.S. Provisional Application No. 60/557,733, filed Mar. 29, 2004.

FIELD OF THE INVENTION

The invention relates to the peptide designated PK2β, which is a processed product from PK2β pro-peptide. PK2β, a selective ligand for PKR1, is useful in treating gastrointestinal disorders (e.g., constipation), lung disorders (e.g., insufficient cilium movement in the lung and airways), and certain cancers (e.g., ovarian cancers and testicular cancers) where PKR1 is expressed.

BACKGROUND OF THE INVENTION

Two cysteine-rich peptides, prokineticin 1 (PK1) and prokineticin 2 (PK2), have been identified. Prokineticins (PKs) are multi-functional peptides, which have been shown to stimulate gastrointestinal (GI) smooth-muscle contractions (Li et al., "Identification of two prokineticin cDNAs: Recombinant proteins potently contract gastrointestinal smooth muscle," *Mol Pharmacol* 59:692-698 (2001)). PK1, also known as endocrine gland vascular endothelial growth factor (EG-VEGF), stimulates proliferation and migration of cells derived from endocrine glands, and promotes angiogenesis in the mouse ovary (LeCouter et al., "Identification of an angiogenic mitogen selective for endocrine gland endothelium," *Nature* 412:877-884 (2001)). PK2, or mammalian Bv8, is believed to affect behavioral circadian rhythms in the suprachiasmatic nucleus (SCN) and promote angiogenesis in the testis (Cheng et al., "Prokineticin 2 transmits the behavioural circadian rhythm of the suprachiasmatic nucleus," *Nature* 417:405-410 (2002); LeCouter et al., "The endocrine-gland-derived VEGF homologue Bv8 promotes angiogenesis in the testis: Localization of Bv8 receptors to endothelial cells," *Proc Natl Acad Sci USA* 100:2685-2690 (2003)).

PK1 and PK2 are closely related and share significant sequence homology to mamba intestinal protein (MIT) (Schweitz et al., "Purification and pharmacological characterization of peptide toxin from the black mamba (*Dendroaspis polylepis*) venom," *Toxicon* 28:847-856 (1990); Schweitz et al., "MIT(1), a black mamba toxin with a new and highly potent activity on intestinal contraction," *FEBS Lett* 461:183-188 (1999)) and a frog skin secreted protein, Bv8. Bv8 is a potent stimulator of GI smooth-muscle contractions (Mollay et al. "Bv8, a small protein from frog skin and its homologue from snake venom induce hyperalgesia in rats," *Eur J Pharmacol* 374:189-196 (1999)) and stimulates the sensitization of peripheral nociceptors (Negri et al., "Nociceptive sensitization by the secretory protein Bv8," *Br J Pharmacol* 137:1147-1154 (2002)).

PKs bind and activate two closely related G-protein coupled receptors (GPCRs), prokineticin receptor 1 (PKR1) and 2 (PKR2), which are 87% identical by sequence (Lin et al., 2002, infra; Masuda et al., "Isolation and identification of EG-VEGF/prokineticins as cognate ligands for two orphan G-protein-coupled receptors," *Biochem Biophys Res Commun* 293: 396-402 (2002); Soga et al., "Molecular cloning and characterization of prokineticin receptors," *Biochim. Biophys. Acta* 1579: 173-179 (2002)). PKs stimulate $Ca^{2+}$ mobilization in PK-receptor (PKR) expressing cells, presumably through receptor $G_q$ protein interaction (Lin et al., "Identification and molecular characterization of two closely related G protein-coupled receptors activated by prokineticin/endocrine gland vascular endothelial growth factor," *J Biol Chem* 277:19276-19280 (2002a)). Pertussis toxin (PTX) inhibits PK1-induced mitogen-activated protein kinase (MAPK) signaling (Lin et al., "Characterization of endocrine gland-derived vascular endothelial growth factor signaling in adrenal cortex capillary endothelial cells," *J Biol Chem* 277:8724-8729 (2002b)), suggesting that PKRs may also couple to $G_i$ proteins.

Sequence alignments have suggested that PKs have distinct N- and C-terminal domains (Bullock et al., "Structural determinants required for the bioactivities of prokineticins and identification of prokinectin receptor antagonists," *Mol. Pharmacology* 65:582-588 (2004)). The N-terminal domain contains six amino acids (AVITGA) conserved among PKs from mammalian and nonmammalian species (id.). The C-terminal region contains ten conserved cysteines forming five pairs of disulfide bridges (id.). The pharmacological activity of a PK2 splice variant containing 21 extra amino acids inserted between exons 2 and 3 has also been studied (id.).

SUMMARY OF THE INVENTION

In one aspect, the invention is directed to a peptide consisting essentially of an amino acid sequence selected from AVITGACDKDSQCGGGMCCAVSIWVKSIRICTPMG-KLGDSCHPLTRKNNFGNGRQE(SEQ.ID.NO.:1)andAVI-TGACDKDSQCGGGMCCAVSIWVKSIRICTPMGQVG-DSCHPLTRKSHVANGRQE (SEQ.ID.NO.:2). In one preferred embodiment, the invention is directed to the human PK2β peptide having an amino acid sequence corresponding to SEQ.ID.NO.:1. In another preferred embodiment, the invention is directed to the mouse or rat PK2β peptide having an amino acid sequence corresponding to SEQ.ID.NO.:2.

In another aspect, the invention is also directed to methods of treating a patient diagnosed with a disease or disorder mediated by PK1 activity, comprising administering a pharmaceutically active amount of a PK2β peptide in substantially pure form. In one preferred embodiment, the disease or disorder is a disease of the gut/intestine or gastrointestinal disorder. In another preferred embodiment, the disease or disorder is a lung disease or disorder.

Various other embodiments, features, and advantages of the invention will be more fully understood by reference to the detailed description and the appended drawing figures.

BRIEF DESCRIPTION OF THE DRAWINGS

FIG. 4A provides the results of the binding assay using PKR1 expressing cells. FIG. 4B shows the results of the binding assay in PKR2 expressing cells (legend: ■, PK1; ▲, PK2; ▼, PK2β).

FIG. 5A shows the results for $Ca^{2+}$ mobilization in PKR1 expressing cells. FIG. 5B provides the results for $Ca^{2+}$ mobilization in PKR2 expressing cells (legend: ■, PK1; ▲, PK2; ▼, PK2β).

DETAILED DESCRIPTION OF THE INVENTION AND ITS PREFERRED EMBODIMENTS

Figure 1:
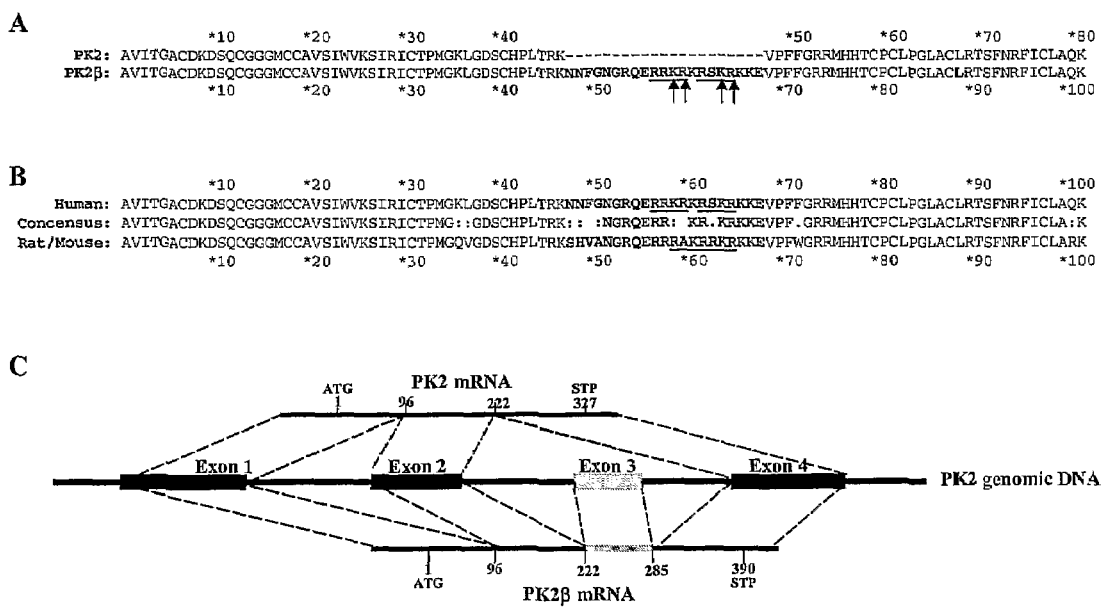
FIG. 1A provides an amino acid sequence comparison between human PK2 (SEQ ID NO.: 27) and the immature PK2β (or PK2L, SEQ ID NO.: 28), without signal peptide (the 21 additional amino acids in PK2L are highlighted in bold letters; the furin recognition sequences are underlined; the potential furin-cutting sites are indicated by arrows).
FIG. 1B shows an amino acid sequence comparison between human and rat/mouse PK2L peptides (SEQ ID NO.: 29) (rat and mouse PK2L peptides are identical; the putative furin recognition sequences are underlined).
FIG. 1C illustrates the gene structure of PK2 and the differential exon usage by PK2 and PK2L mRNA (the numbers indicate the nucleotide positions in PK2 and PK2L coding regions, respectively; ATG and STP represent the translation start and stop codons, respectively).

The cDNA for an alternatively spliced PK2 mRNA, designated herein as PK2L, encodes 21 additional amino acids compared with PK2. It has now been discovered that the expression of PK2L results in the production of a short form of the peptide designated herein as PK2β.

Functional characterization of PK2β in comparison with PK1 and PK2 indicates that PK2β displays strong receptor selectivity for PKR1 versus PKR2. In addition, signal transduction studies show that PKs stimulate adenyl cyclase in PKR expressing cells, indicating that PKRs are also coupled to $G_s$ proteins.

As described in the examples below, PK2L was recombinantly expressed in mammalian cells and pharmacologically characterized in comparison with PK1 and PK2. Biochemical characterization indicates that secreted PK2L protein is further processed to a smaller peptide by proteolytic cleavage, presumably by cleavage at the two putative furin cleavage sites, designated PK2β. Co-expression of furin with PK2L increased the PK2β processing efficiency significantly. Functional studies showed that PK1, PK2, and PK2β peptides stimulate intracellular $Ca^{2+}$ response in PKR1-expressing cells with similar potencies. However, PK2β stimulus of $Ca^{2+}$ response in PKR2-expressing cells is approximately 50-fold less potent than PK1 and PK2. The differential stimulus of $Ca^{2+}$ response by PK2β compared to PK2 on cells expressing PKR1 and PKR2, combined with different expression pattern of PK2 and PK2L, indicates that these peptides might have different functions in vivo. The results, which are discussed below, indicate that PKs not only stimulate $Ca^{2+}$ mobilization, but also induce cAMP accumulation in PKR-expressing cells. Functional expression and purification of PK2β provides a useful agent for selective activation of PKR1 in vivo. Thus, PK2β should be useful as a therapeutic to selectively activate PKR1. The selective activation of PKR1 by PK2β also facilitates the identification and screening of compounds that bind to or modulate activity of PK2β, or are PK2β binding competitors, so as to up-regulate or down-regulate PKR1 activity, which compounds may be used (e.g., as inhibitors, agonists, or antagonists of PK2β activity) in treating diseases or disorders mediated by PKR1 activity.

Exemplary medical conditions, diseases, or other indications that may be treated with the peptide of the invention or compounds that modulate its activity include, but are not limited to, treatment to improve gastrointestianal (GI) function and motility, pulmonary and lung function, immune function, placental function, vascular function, pre- and post-natal nutrition, circadian rhythms, and milk production. Exemplary lung diseases include asthma, sarcoidosis, interstitial lung disease, interstitial pneumonia, Sjogren syndrome, bronchiolitis obliterans syndrome (BOS), fibrotic lung disease, chronic obstructive pulmonary disease (COPD), and acute respiratory distress syndrome (ARDS) (see, e.g., Efthimiou et al, 2005, *South Med. J.*, 98(2):192-204; Hachem et al., 2004, *Semin. Thorac. Cardiovasc. Surg.*, 16(4):350-355; and Medford et al., 2005, *Thorax.*, 60(3):244-248). Exemplary GI diseases include irritable bowel syndrome, diabetic gastroparesis, postoperational ileus, chronic constipation, gastroesophageal reflux disease, chronic dyspepsia, and gastroparesis (see, e.g., Samsom et al., 1997, *Dig. Dis.* 1997, 15(4-5):263-274; Tonini et al, 1996, *Pharmacol. Res.*, 33(4-5):217-226; Achem et al., 1998, *Dig. Dis.*, 16(1): 38-46; and Briejer et al, 1999, *Trends Pharmacol. Sci.* 20(1): 1-3). Exemplary pregnancy and placental function-related disorders include placental dysfunction, preeclampsia, fetal inflammatory response syndrome, and antiphospholipid syndrome (LPS) (see, e.g., Weissgerber et al., 2004, *Med. Sci. Sport.s Exerc.*, 36(12):2024-2031; Arad et al., 2004, *Isr. Med. Assoc. J.*, 6(12):766-769; and Hickey et al., 2000, *Baillieres Best Pract. Res. Clin. Obstet. Gynaecol.*, 14(6):937-51). Exemplary diseases associated with aberrant regulation of angiogenesis include certain cancers, such as, ovarian cancers, cervical cancers, testicular cancers, and adrenal cancers (see, e.g., LeCouter et al., 2002, *Cold Spring Harb. Symp. Quant. Biol*, 67:217-221; Kisliouk et al., 2003, *J. Clin. Endocrinol. Metab.*, 88(8):3700-3707; LeCouter et al, 2003, *Proc. Natl. Acad. Sci. USA.*, 100(5):2685-2690; Zhang et al., 2003, *Clin. Cancer Res.*, 9(1):264-272; LeCouter et al., 2002, *Nat. Med.*, 8(9):913-917; Ferrara et al., 2003, *Am. J. Pathol.*, 162 (6):1881-1893; and LeCouter et al., 2003, *Endocrinology*, 144(6):2606-2616). The appropriate dosage or effective amount for treating such diseases, medical conditions, or other indications may be routinely determined using known techniques for determining appropriate dosages.

The preparation of PK2β material, which may be used as a therapeutic or for identifying therapeutic compounds, is illustrated below.

Materials and Methods cDNA Cloning of PKR1 and PKR2. The full-length cDNA coding regions for both PKR1 and PKR2 were PCR-amplified from human fetal brain cDNA (Clontech, Palo Alto, Calif.). The primers used for PKR1 were P1: 5' ACG TGA ATT CGC CAC CAT GGA GAC CAC CAT GGG GTT CAT G 3' (SEQ.ID.NO.:3), and P2: 5' ACG TAG CGG CCG CTT ATT TTA GTC TGA TGC AGT CCA CCT C3' (SEQ. ID.NO.:4). The primers used for PKR2 were P3: 5' ACG CGA ATT CGC CAC CAT GGC AGC CCA GAA TGG AAA CAC 3' (SEQ.ID.NO.:5), and P4: 5' ACG CAT GCG GCC GCG TCA CTT CAG CCT GAT ACA GTC CAC 3' (SEQ.ID.NO.:6). The PCR (polymerase chain reaction) conditions were 94° C. for 40 seconds (s), 65° C. for 40 s and 72° C. for 3 minutes (min) (40 cycles). The PCR products were cloned into pCIneo (Promega, Madison, Wis.) vector and the insert regions were sequenced using an automated DNA sequencer (ABI, Foster City, Calif.).

Expression and Purification of Prokineticins. Human PK1 mature peptide coding region was PCR amplified from human fetal brain cDNA (Clontech) using two primers P5: 5 TCA TCA CGA ATT CGA TGA CGA CGA TAA GGC TGT GAT CAC AGG GGC CTG TGA GCG GGA TG 3' (SEQ. ID.NO.:7), and P6: 5' ACG ATA GGA TCC CTA AAA ATT GAT GTT CTT CAA GTC CAT G 3' (SEQ.ID.NO.:8). Human PK2 and PK2L cDNAs without signal peptide coding region were PCR amplified from human fetal brain cDNA (Clontech) using two primers P7: 5' CAT CAC GAA TTC GAT GAC GAC GAT AAG GCC GTG ATC ACC GGG GCT TGT GAC AAG 3' (SEQ.ID.NO.:9) and P8: 5' ACG ATA GGA TCC TTA CTT TTG GGC TAA ACA AAT AAA TCG 3' (SEQ.ID.NO.:10). The PCR conditions were 94° C. for 40 s, 65° C. for 40 s and 72° C. for 1 min (40 cycles). The PCR products for PK1, PK2, and PK2L were cloned into a modified pCMV-sport1 (Invitrogen) expression vector, which encodes an alpha peptide signal sequence followed by a FLAG tag. The PK cDNAs were cloned in-frame after the FLAG coding sequence and the insert regions were sequenced to confirm the identities. The resulting expression vectors encoded chimeric proteins with a mammalian secreted protein signal peptide followed by a FLAG peptide, an enterokinase cleavage site, and PK1, PK2 and PK2L without their natural signal peptide sequences, respectively. The PK1, PK2 and PK2L plasmids were transfected into COS-7 cells using LipofectAmine (Invitrogen). Three days after transfection, the cell culture supernatants were collected and run through ANTI-FLAG M2 agarose (Sigma, St. Louis, Mo.) affinity columns. The columns were washed with phosphate-buffered saline (PBS) and eluted with 0.1 mM Glycine HCl, pH 3.0. The eluted protein fractions were immediately neutralized with 1 M Tris-HCl, pH 8.0 and cleaved with enterokinase (Novagen, Madison, Wis.). The cleaved proteins were then further purified by reverse-phase high-performance liquid chromatography (HPLC) using a C4 column (Vydac, Hispevia, Calif.).

Western Blot. Recombinant PK protein expression was monitored by Western Blot. In a 1.5 ml tube, 20 µl of ANTI-FLAG M2 agarose beads slurry were added to 1 ml of cell culture media from COS-7 cells expressing PK1, PK2, PK2L, co-expressing PK2L and furin, or from control COS-7 cells. At the same time, corresponding cell samples were lysed with lysis buffer (100 mM Tris-HCl, pH 8.0, 150 mM NaCl, 1% Triton X-100, 1% protease inhibitor cocktail, Sigma) and mixed with the ANTI-FLAG beads. The tubes were incubated at 4° C. on a rocking platform overnight. The beads were centrifuged and washed twice with ice cold TBST (50 mM Tris-HCl pH 7.5, 150 mM NaCl, 0.05% Tween 20). The immuno-precipitated proteins were run onto a 4-20% SDS-PAGE gel under reducing conditions and transferred onto a PVDF membrane (Invitrogen). The membrane was blotted first with ANTI-FLAG M2 antibody (Sigma) and then with goat anti-mouse IgG (horseradish peroxidase conjugated, Sigma). The Western blot membrane was then developed with an Amersham ECL kit.

Expression, purification, and iodination of C-terminal FLAG-tagged PK2. C-terminal FLAG-tagged PK2 (PK2-f) was constructed as described (Soga et al., 2002). Two primers P9: ATC GAG AAT TCG CCA CCA TGA GGA GCC TGT GCT GCG CCC (SEQ.ID.NO.:11) and P10: GGA TCC CTA CTT ATC GTC GTC ATC CTT ATA ATC CTT TTG GGC TAA ACA (SEQ.ID.NO.:12) were used to amplify human whole brain cDNA (Clontech). The PCR-amplified PK2-f was cloned into a mammalian expression vector pCMV-sport1 (Invitrogen). The resulting clones were sequenced to confirm the identities and transfected into COS-7 cells using LipofectAmine (Invitrogen). Three days after transfection, the cell culture supernatant was collected and run through an ANTI-FLAG M2 agarose (Sigma) affinity column. The column was washed with PBS and eluted with 0.1 mM Glycine HCl, pH 3.0. The eluted protein fraction was immediately neutralized with 1 M Tris-HCl, pH 8.0 and then further purified by reverse-phase HPLC using a C4 column (Vydac). The purified recombinant PK2-f protein was iodinated using Iodogen reagent (Pierce, Rockford, Ill.) and $^{125}$I-NaI (PerkinElmer, Boston, Mass.) as described by Pierce. The iodinated PK2-f was purified by a G-50 (Amersham Pharmacia Biotech) gel filtration column.

Radio-Ligand Binding Assays. PKR1 and PKR2 in the expression vector pCIneo (Promega) were transfected into COS-7 cells using LipofectAmine (Invitrogen). Two days after transfection, cells were detached from the culture dishes by 10 mM EDTA in PBS, washed with Dulbecco's Modified Eagle's Medium (DMEM) and seeded in 96-well opaque polylysine-coated plates (BD Biosciences, San Jose, Calif.) at a density of 50,000 cells per well. Two hours after the seeding, competition binding assays were carried out in the 96-well plates at presence of 100 pM $^{125}$I-labeled PK2-f and various concentrations of unlabeled PK1, PK2 or PK2β as competitors. The binding assays were performed in DMEM plus 50 mM HEPES, pH 7.2 and 1% bovine serum albumin in a final volume of 100 µl. The binding assays were carried out at room temperature for 1 hour. After the plates were washed three times with ice cold PBS, Microscint-40 (Packard, Meriden, Conn.) was added and the plates were counted on a Topcount (Packard).

Intracellular $Ca^{2+}$ Mobilization Assays. PKR1 and PKR2 in the expression vector pCIneo (Promega) were transfected into HEK293 cells using LipofectAmine (Invitrogen). Two days after transfection, cells were detached using PBS containing 10 mM EDTA and seeded in poly-D-lysine coated 96-well black tissue culture plates (BD Biosciences). Ligand stimulated $Ca^{2+}$ mobilization was assayed using Fluo-3 $Ca^{2+}$ dye (TEF Labs, Austin, Tex.) in FLIPR (Molecular Devices, Sunnyvale, Calif.) as described previously (Liu et al., "Comparison of human, mouse, rat and guinea pig histamine H4 receptors reveals substantial pharmacological species variation," *J Pharmacol Exp Ther* 299:121-130 (2001a)).

Stimulation of cAMP accumulation in PKR expressing cells by PKs. PK stimulated cAMP accumulation assays were performed using PKR1 and PKR2 stably expressing SK-N-MC cells carrying a β-galactosidase reporter gene under the control of CRE promoter. The stable cell lines were created under selection of 400 mg/L G418 (Sigma) following the transfection of PKR1 or PKR2 expression vectors. Increase of the intracellular cAMP concentration leads to higher β-galactosidase expression, whose activity is measured using chlorophenol red-β-D-galactopyranoside (CPRG) as the substrate. Cells were seeded in 96-well tissue culture plates, stimulated with different concentrations of PK1, PK2 or PK2β. Intracelluar cAMP concentrations were indirectly measured by assaying the β-galactosidase activities in the cells as described (Liu et al., "Cloning and pharmacological characterization of a fourth histamine receptor (H4) expressed in bone marrow," *Mol Pharmacol* 59:420-426 (2001b)).

In a different experiment, PKR1 and PKR2 in the expression vector pCIneo (Promega) were co-transfected with the $G_s$ expression plasmid into HEK293 cells using LipofectAmine (Invitrogen). Two days after transfection, cells were detached with 10 mM EDTA in PBS, resuspended in Dulbecco's Modified Eagle's Medium/F12 (DMEM/F12) media, and then plated on 96-well plates at a density of 50,000 cells per well. Two hours after the seeding, cells culture medium was replaced with DMEM/F12 containing 2 mM isobutylmethylxanthine (Sigma) and incubated for 30 min. Different concentrations of PK1, PK2 or PK2β were added to cells and incubated for an additional 30 min in a final volume of 200 μl/well. The reaction was stopped and cAMP was extracted by adding 20 μl of 0.5 N HCl to each well. Cell culture media were tested for cAMP concentrations by the cAMP [$^{125}$I] FlashPlate Assay kit (PerkinElmer) as described by the manufacturer.

RT-PCR detection of PK2L mRNA expression in different human tissues. Eleven human cDNA pools (Clontech) from human tissues were analyzed for mRNA expression for PK1, PK2, PK2β, PKR1 and PKR2 using PCR amplification method. The PCR primers used in the reactions are P7 and P8 as described above for PK2 and PK2β; P11: 5'ACG TAA GAA TTC GCC ACC ATG AGA GGT GCC ACG CGA GTC TCA3' (SEQ.ID.NO.:13) and P12: 5'ACG TAA GAA TTC CTA AAA ATT GAT GTT CTT CAA GTC CAT GGA3' (SEQ.ID.NO.:14) for PK1; P13: 5'CAA CTT CAG CTA CAG CGA CTA TGA TAT GCC TTT GG3' (SEQ.ID.NO.: 15) and P14: 5'GAC GAG GAC CGT CTC GGT GGT GAA GTA GGC GGA AG3' (SEQ.ID.NO.:16) for PKR1; and P15: 5'TCT CCT TTA ACT TCA GTT ATG GTG ATT ATG ACC TC3' (SEQ.ID.NO.:17) and P16: 5'CGA TGG GAT GGC AAT GAG AAT GGA CAC CAT CCA GA3' (SEQ.ID.NO.: 18) for PKR2. All the PCR reaction were performed at the conditions of 94° C. for 40 sec, 65° C. for 30 sec, 72° C. for 1 min, for 40 cycles using Platinum Taq DNA polymerase (Invitrogen). The PCR products were run on agarose gels, transferred onto nitrocellulose membranes and hybridized with $^{32}$P-labeled oligo probes specific for PK1 (5'ACC TGT CCT TGC TTG CCC AAC CTG CTG TGC TCC AGG TTC3'—SEQ.ID.NO.:19), PK2 and PK2β (5'TGG GCA AAC TGG GAG ACA GCT GCC ATC CAC TGA CTC GTA3'—SEQ.ID.NO.:20), PKR1 (5'CTG ATT GCC TTG GTG TGG ACG GTG TCC ATC CTG ATC GCC ATC C3'— SEQ.ID.NO.:21), and PKR2 (5'CGG ATG AAT TAT CAA ACG GCC TCC TTC CTG ATC GCC TTG G3'— SEQ.ID.NO.:22), respectively. PCR detection for human β-actin gene expression was used for all tissue as a control for the quality of the cDNAs. The primers for PCR detection of human β-actin mRNA expression were 5'GAG AAG AGC TAC GAG CTG CCT GAC GGC CAG GTC3' (SEQ.ID.NO.: 23) and 5'AAG GGT GTA ACG CAA CTA AGT CAT AGT CCG CCT A 3' (SEQ.ID.NO.:24).

Results

Identification of PK2L cDNA and molecular characterization of PK2L mRNA tissue expression pattern. In the course of characterizing the PK2 mRNA tissue expression profile using RT-PCR, a PCR product with slightly larger size than the predicted PK2 PCR product was identified. Molecular cloning and DNA sequencing of that PCR product indicated that it has a 63 base pair insertion to the coding region of PK2, which results in a protein 21 residues longer (FIG. 1A) and is designated as PK2L. Genbank search indicated that our sequence encodes a protein that is identical to a protein sequence in NCBI protein database (Genbank Accession Number Q9HC23, Wechselberger, et al., "The mammalian homologues of frog Bv8 are mainly expressed in spermatocytes," *FEBS Lett* 462:177-181 (1999)). Using a similar method, a rat PK2L cDNA was also isolated from rat lung cDNA pool. The complete cDNA sequences for human and rat PK2L have been submitted to Genbank (Genbank Accession Number: AY349131; AY348322). Protein sequence comparison indicates that the rat and mouse (Genbank Accession Number: NP_056583) PK2L proteins are essentially identical, with exception of the signal sequences, and are highly related to human PK2L with 90% amino acid identity (FIG. 1B).

Figure 2:
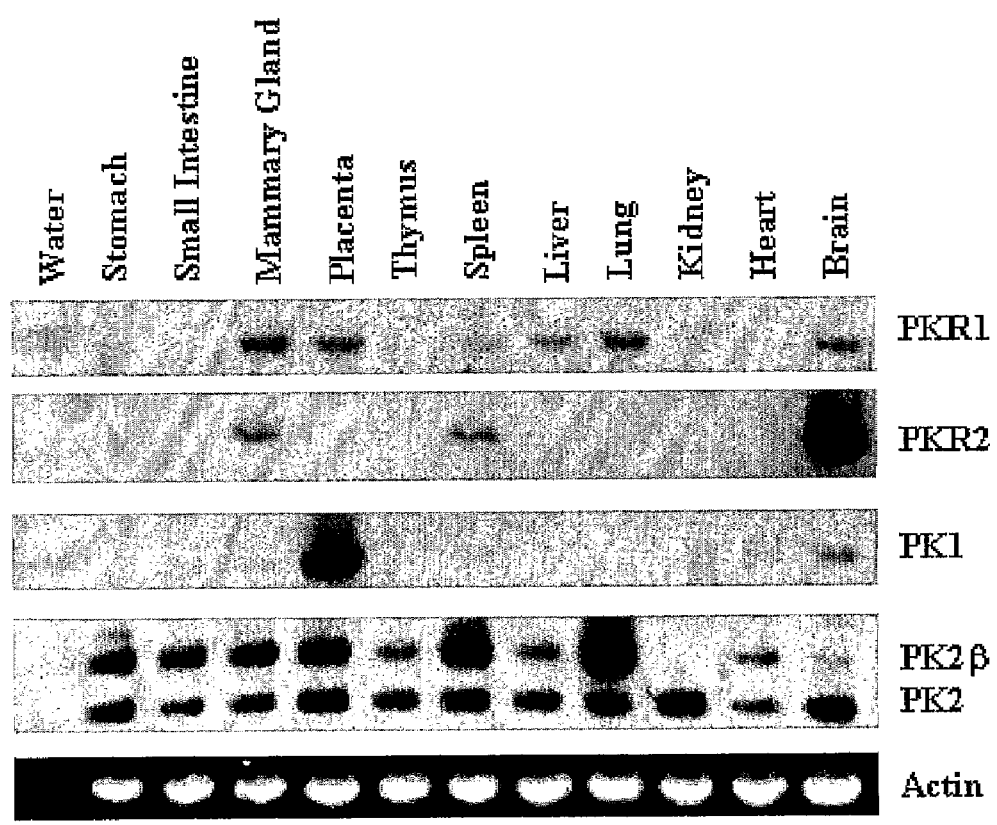
FIG. 2 depicts the mRNA expression profiles of PKs and PKRs. RT-PCR products for PKR1, PKR2, PK1, PK2 and PK2L were run in agarose gels transferred to nitrocellulose membrane and hybridized with specific probes, respectively. RT-PCR detection of human β-actin mRNA expression was used as an internal control.

DNA sequence comparison among human PK2, PK2L and genomic DNA shows that the PK2 gene contains a putative exon region that is not used by PK2 (FIG. 1C), indicating that PK2L mRNA may be an alternatively spliced isoform from the PK2 gene. The mRNA expression profile of PK2L was analyzed in parallel with that of PK1, PK2, PKR1 and PKR2 in 11 different human tissues using RT-PCR method. As shown in FIG. 2, the results indicate that each of them has its unique expression pattern. PK1 mRNA is found mainly expressed in placenta while PK2 mRNA is found in all tissues. PK2L mRNA was detected in most tissues tested and was found to be highest in lung and spleen, barely detected in brain and not detectable in kidney, where PK2 mRNA is detected. PKR1 mRNA was detected in brain, lung, liver, spleen, spleen, and mammary gland. PKR2 mRNA has a very dominant expression in the brain with lower levels of expression in spleen and mammary gland.

Expression, purification, and biochemical characterization of PKs. PK1, PK2 and PK2L were expressed as secreted fusion proteins with a N-terminal FLAG tag from COS-7 cells. The secreted fusion proteins in cell culture supernatants were purified using ANTI-FLAG M2 affinity columns. The affinity-purified proteins were cleaved with enterokinase, and further purified by reverse-phase HPLC. The HPLC-purified proteins are greater than 98% pure. The sizes of PK1 (10 kDa) and PK2 (9 kDa) agree with our prediction. However, the size of purified protein from COS-7 cells expressing PK2L (6-7 kDa) is much smaller than what was predicted (11.5 kDa) according to the PK2L cDNA coding region. Since the PK2L coding region encodes 21 additional amino acids compared with PK2, we expected that PK2L should have a higher molecular weight (MW) than PK2. However, the purified protein PK2L cDNA transfected COS-7 cells has a MW smaller than PK2, indicating that there is a pro-protein cleavage process for PK2L protein.

Figure 3:
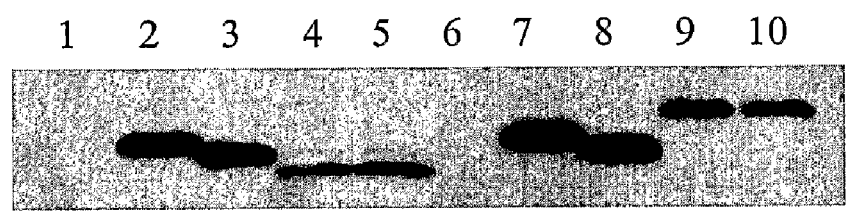
FIG. 3 shows the results of Western blot analysis of recombinant PKs expressed in COS-7 cells (FLAG-tagged PK1, PK2 and PK2L either from cell conditioned media (lanes 1-5) or from cell lysates (lanes 6-10), which were analyzed by Western Blot using anti-FLAG M2 antibody; lanes 1 and 6 show control cells, lanes 2 and 7 show results of cells expressing PK1, lanes 3 and 8 show cells expressing PK2, lanes 4 and 9 show cells expressing PK2L, and lanes 5 and 10 show cells co-expressing PK2L and furin).

Western blot analysis of the PK2L expressing cell lysate and cell culture medium indicated that FLAG-PK2L was made in the cells as predicted size (13.5 kDa), which is bigger than FLAG-PK1 (11.7 kDa) and FLAG-PK2 (10.8 kDa) (FIG. 3). Although trace amounts of FLAG-PK2L were detected in the culture medium, the majority of FLAG-PK2L present in the conditioned medium appears to be processed into a smaller form, namely PK2β (8-9 kDa) (FIG. 3). Based on the size of PK2β, the protease cleavage site is predicted in the stretch of 21 additional amino acids present in FLAG-PK2L. The majority of those 21 amino acids are basic amino acids, thus forming a sequence with a few putative pro-hormone convertase cleavage sites, including two furin sites. The doublet bands of the processed FLAG-PK2β indicate the differential process of the FLAG-PK2L at the two different furin cleavage sites. Since furin is expressed in many different cells including COS-7, furin may be responsible for the cleavage of PK2L. Co-expression of additional furin with PK2L leads to the complete processing of PK2L into PK2β (FIG. 3). The lower band of the PK2β was the majority of the processed form and was further purified by reverse-phase HPLC and used for pharmacological characterizations.

Figure 4A:
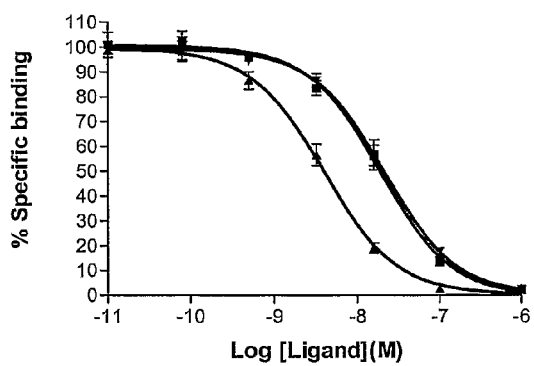
FIGS. 4A and 4B graphically illustrate that PKs bind the PKR1 and PKR2 with different affinities. COS-7 cells transiently expressing PKR1 or PKR2 were seeded to 96-well plates. $^{125}$I-labeled PK2-f was added to each well at a final concentration of 100 pM. Different concentrations of PK1, PK2 or PK2β were added to the assays as the competitors. All assays were performed in triplicates. The results are mean values (±S.E.M) of triplicates.
Figure 4B:
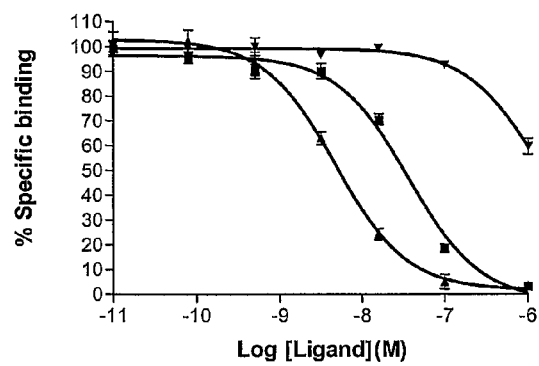

Prokineticins bind PKR1 and PKR2 with different affinities. With the purified PK2β available, it was investigated whether PK2β binds PKR1 or PKR2 in comparison with PK1 and PK2. C-terminal FLAG-tagged PK2 was labeled with $^{125}I$ and used as the radioligand, which has been reported to bind prokineticin receptors at high affinity (Soga et. al., 2002). Membranes from COS-7 cells transiently expressing PKR1 and PKR2 were used in competition binding assays. The results (FIG. 4A) indicate that PK1, PK2, and PK2β all bind PKR1 with high affinities, with the rank order of potency PK2>PK2β≅PK1. For PKR2, only PK1 and PK2 showed high affinity in the binding assays, whereas PK2β was marginal active at high concentrations (FIG. 4B). The ligand rank order of potency for PKR2 is PK2>PK1>>PK2β. The $IC_{50}$ values of PK1, PK2, and PK2β for PKR1 and PKR2 are listed in Table 1.

TABLE 1

Comparison of $IC_{50}$ values[a] of PK1, PK2 and PK2β on PKR1 and PKR2

|  | PKR1 | PKR2 |
|---|---|---|
| PK1 | 27.6 ± 8.2 | 52.2 ± 16.4 |
| PK2 | 4.5 ± 0.8 | 6.4 ± 1.3 |
| PK2β | 34.6 ± 13.5 | >1,000 |

[a]$IC_{50}$ values were expressed as nM (mean ± S.E.) from triplicate experiments in radioligand competition binding assays.

Figure 5A:
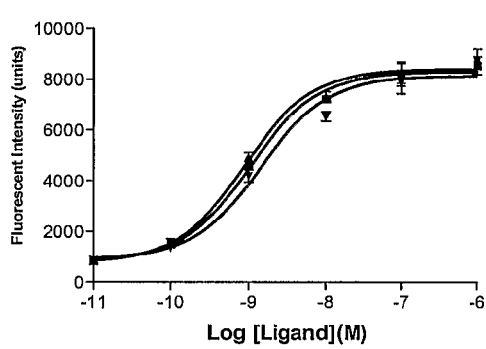
FIGS. 5A and 5B graphically illustrate that PKs stimulate $Ca^{2+}$ mobilization in HEK 293 cells expressing PKR1 or PKR2 at different potencies. HEK 293 cells transiently expressing PKR1 or PKR2 were seeded in 96-well plates, loaded with $Ca^{2+}$ dye Fluo-3 and then stimulated with different concentrations of PK1, PK2 or PK2β. The release of $Ca^{2+}$ was measured with a fluorescence imaging plate reader (FLIPR). The results are mean values (±S.E.M) of triplicate experiments.
Figure 5B:
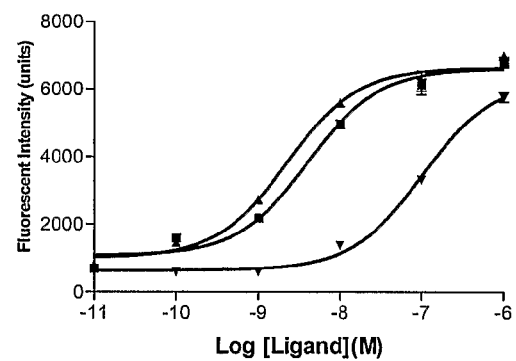

PK2β selectively activates PKR1. PK1 and PK2 have been reported to stimulate $Ca^{2+}$ mobilization in PKR expressing cells (Lin et. al., 2002a; Soga et. al., 2002). This study was designed to compare PK1, PK2 and PK2β in stimulation of $Ca^{2+}$ mobilization in PKR expressing cells. The results show that PK1, PK2 and PK2β stimulate $Ca^{2+}$ mobilization in PKR1 expressing HEK293 cells at nanomolar concentrations (FIG. 5A). Unlike PK1 and PK2, which have high potency for both receptors, PK2β is only active at PKR1 (FIGS. 5A, 5B), consistent with the binding results. The $EC_{50}$ for all $Ca^{2+}$ assays are summarized in Table 2.

TABLE 2

$EC_{50}$ values[a] of PK1, PK2 and PK2β for $Ca^{2+}$ mobilization in PKR expressing HEK 293 cells

|  | PKR1 | PKR2 |
|---|---|---|
| PK1 | 1.1 ± 0.4 | 7.7 ± 2.1 |
| PK2 | 0.8 ± 0.23 | 3.6 ± 1.6 |
| PK2β | 1.5 ± 0.56 | 80 ± 9.7 |

[a]values were expressed in nM (mean ± S.E.) from triplicate experiments.

Figure 6:
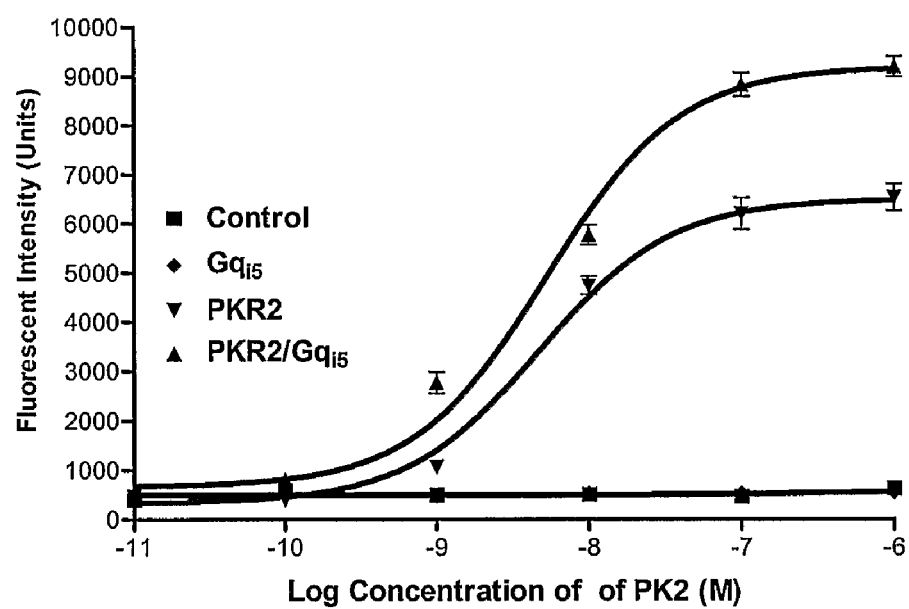
FIG. 6 shows that $Gq_{i5}$ enhances PK induced $Ca^{2+}$ mobilization in PKR2 expressing 293 cells. The 293 cells were transfected either with $Gq_{i5}$ or PKR2, or co-transfected with PKR2 and $Gq_{i5}$. Two days after transfection, the cells were tested in $Ca^{2+}$ mobilization assays in response to PK2 stimulation.

Prokineticin receptors are coupled to multiple signal transduction pathways. It has been reported that PTX inhibits PK stimulated MAP kinase signaling (Lin et al., 2002b), suggesting that PKR activates MAP kinase through activation of $G_i$-related proteins. In conducting the $Ca^{2+}$ mobilization assays it was observed that the maximum ligand stimulated $Ca^{2+}$ mobilization in PKR2 expressing cells is consistently significantly lower than that in PKR1 expressing cells, which is consistent with what has been reported (Lin et al., 2002a). However, when PKR2 was co-expressed with a chimeric G protein $G_{qi5}$, which shifts receptor/$G_i$ coupling to $Ca^{2+}$ mobilization signaling (Conklin et al., "Substitution of three amino acids switches receptor specificity of Gqα to that of Gα," Nature 363:274-280 (1993)), the maximum ligand stimulated $Ca^{2+}$ mobilization in PKR2 expressing cells increased (FIG. 6) to approximately the same level of that from PKR1 expressing cells, suggesting that PKR2 may also be coupled with $G_i$ related G-proteins, in agreement with the earlier report by Lin et al. (2002b). Other data obtained showed that the $Ca^{2+}$ mobilization in PKR1 expressing cells is not significantly affected by co-expression of $G_{qi5}$.

Figure 7A:
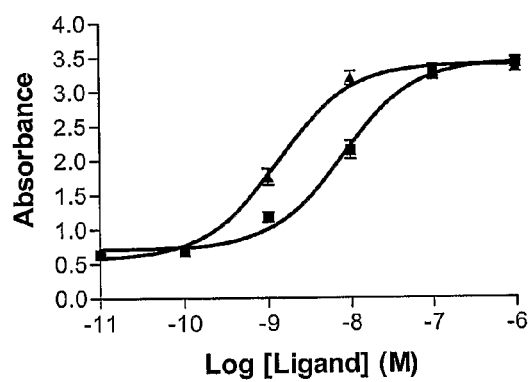
FIGS. 7A and 7B depict experimental results showing that prokineticins stimulate cAMP accumulation in PKR1 (FIG. 7A) and PKR2 (FIG. 7B) expressing SK-N-MC/β-gal cells. Cells were seeded in 96-well plates the night before the assay. Different concentrations of PK1 or PK2 were added to the medium and incubated at 37° C. for 6 hours (h). The cAMP concentrations were measured by assaying the β-galactosidase activity in the cells using CPRG as the substrate. The assays results were read in a microplate reader at 570 nm (legend: ■, PK1; ▲, PK2; ▼, PK2β).
Figure 7B:
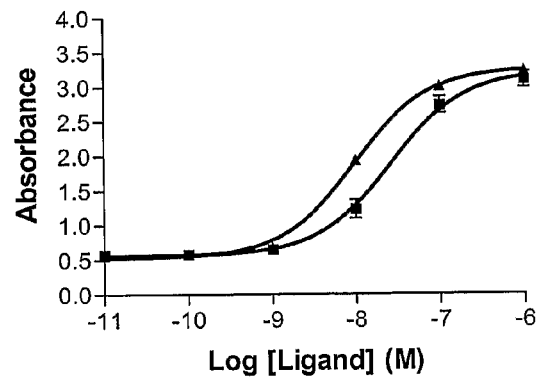

To further investigate the signal transduction pathways used by PKR1 and PKR2, the effects of the PKs on the stimulation of cAMP accumulation in PKR1 and PKR2 expressing cells were examined. PKR1 and PKR2 cell lines were established in SK-N-MC cells harboring a β-galactosidase gene under control of CRE promoter (Liu et al. 2001b). In the host cells, increase of cAMP concentration led to increased β-galactosidase expression, whose enzyme activity, which reflects the cAMP concentration in the cells, was measured using CPRG as the substrate. The results indicated that PK1 and PK2 stimulated β-galactosidase activity in PKR expressing cells in dose-dependent manners (FIG. 7A, 7B). Other data obtained demonstrated that, without PKR expression, SK-N-MC cells showed no response to PKs. The $EC_{50}$ values for PKs to stimulate β-galactosidase activity in PKR expressing cells are shown in Table 3.

TABLE 3

$EC_{50}$ values of PK1, PK2 and PK2β for stimulation of cAMP accumulation in PKR expressing cells

| | SK-N-MC cells | | HEK 293 cells | |
|---|---|---|---|---|
|  | PKR1 | PKR2 | PKR1 | PKR2 |
| PK1 | 8.34 ± 2.3[a] | 20 ± 4.2 | 16.8 ± 3.4 | 60 ± 6.5 |
| PK2 | 1.27 ± 0.4 | 12.1 ± 2.8 | 3.17 ± 1.6 | 41 ± 5.3 |
| PK2β | ND[b] | ND | 23.4 ± 4.4 | >1,000 |

[a]$EC_{50}$ values were expressed as nM (mean ± S.E.) of triplicate experiments.
[b]ND: not determined.

Figure 8A:
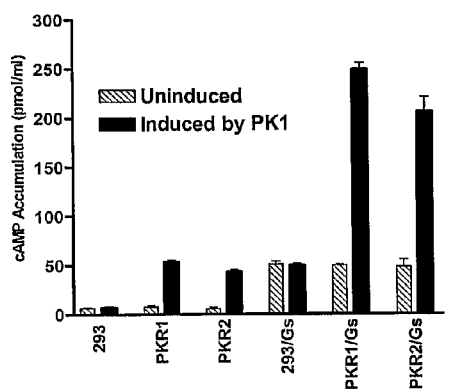
FIG. 8A shows results demonstrating stimulation of cAMP accumulation in PKR1 and PKR2 expressing cells (HEK293 cells were either mock transfected or transfected by PKR1, PKR2, Gs or co-transfected by Gs with PKR1 or PKR2; the transfected cells were stimulated by 1 μM of PK2; the accumulated cAMP was measured using cAMP [$^{125}$I] FlashPlate Assay kit).
Figure 8B:
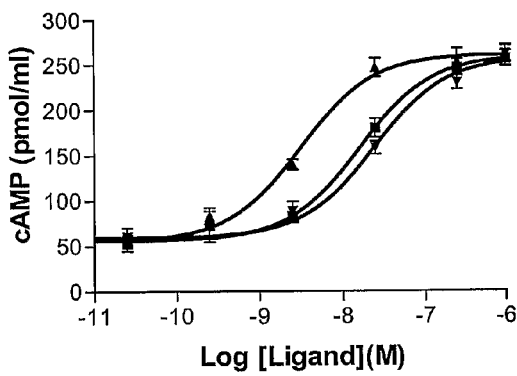
FIGS. 8B and 8C illustrate results from HEK 293 cells co-expressing PKR1/Gs (FIG. 8B) or PKR2/Gs (FIG. 8C) stimulated with different PKs at various concentrations (the accumulated cAMP was measured by a cAMP [$^{125}$I] FlashPlate Assay kit; the results are mean values (±S.E.M) of triplicate experiments (legend: ■, PK1; ▲, PK2; ▼, PK2β)).
Figure 8C:
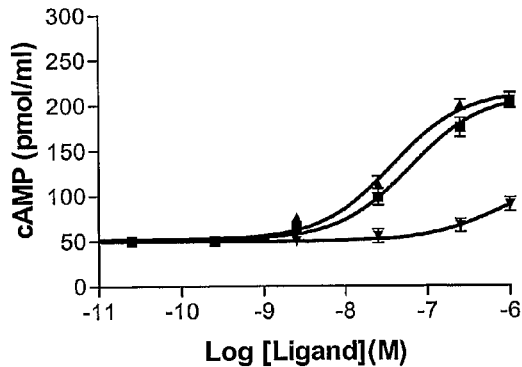

The cAMP accumulation assays were performed in HEK293 cells transiently expressing PKR1 or PKR2. The results indicated that PK stimulates cAMP accumulation in PKR expressing cells. The ligand stimulated cAMP accumulation is significantly increased if the $G_s$ protein is co-expressed with PKRs (FIG. 8A). In the cAMP accumulation assays, the rank order of potency for PK1, PK2, and PK2β is similar to that from the $Ca^{2+}$ assays. All PKs showed high potencies for PKR1 (FIG. 8B). For PKR2 expressing cells, only PK1 and PK2 appeared to be high-potency ligands, PK2β only showed marginal activity at high concentrations (FIG. 8C). HEK293 cells without PKR expression did not respond to PK stimulation. The $EC_{50}$ values for PKs in stimulation of cAMP accumulation in PKR1 or PKR2 expressing cells HEK293 cells are shown in Table 3.

Discussion

Analysis of the gene structure of PK2 indicates that the putative alternative splicing occurs in the third exon of the PK2 gene. Compared to PK2, PK2L mRNA has an additional exon (63 bp) leading to a 21 amino acid insertion between $Lys^{47}$ and $Val^{48}$ of the PK2 protein. A very similar splice variant was also found in the rat and has been reported in the mouse (Wecheselberger et al., 1999), and therefore the function of PK2L appears to be conserved among species. The mRNA expression analysis of PK2L indicates that the PK2L mRNA expression pattern is different from that of PK2, and therefore PK2L may function differently. The relatively abundant PK2L mRNA expression in lung and spleen, where PKR1 mRNA is also expressed, indicates that PK2L may participate some lung and immune functions. PKs are known to stimulate smooth muscle contractions. The high level of PK2L mRNA expression may be related to activation of the cilium movement in the lung to repel the dust particles and fluid out of the lung. A chemoattractive effect of PKs has been shown for adrenal cortical capillary endothelial (ACE) cells expressing PKR (LeCouter et al., 2003). The high level of PK2L expression in the spleen raises the interest to see whether immune cells express PKR and chemoattract in responses to PKs.

To investigate the functional roles of PK2L, PK2L cDNA was expressed in mammalian cells in parallel with PK1 and PK2 and the expressed proteins were purified. The recombinant peptides were made by expressing the FLAG-tagged proteins, cleaving away the tags, and purifying the final products by HPLC. While the final products for PK1 and PK2 expression were as we expected, the purified peptide from cells expressing PK2L cDNA was surprisingly smaller than we expected. Comparison of PK2L peptides in the cell lysate (unsecreted) and the medium (secreted) indicated that PK2L is made in the cells as expected but is further processed into the smaller form by proteolytic cleavage. Protein sequence analysis of PK2L indicated that there exist two putative furin cleavage sites (Arg-Arg-Lys-$Arg^{60}$, SEQ ID NO.: 25, and Arg-Ser-Lys-$Arg^{65}$, SEQ ID NO.: 26), which fit the Arg-X-Lys-Arg or Arg-X-Arg-Arg motif for furin cleavage sites (Steiner et al., "The new enzymology of precursor processing endoproteases," *J Biol Chem* 267: 23435-23438 (1992); Nakayama, "Furin: a mammalian subtilisin/Kex2p-like endoprotease involved in processing of a wide variety of precursor proteins," *Biochem J* 327: 625-635 (1997)). The similar furin cleavage sites are also present in mouse and rat PK2L, but are absent in PK1 and PK2 peptides. Since furin is expressed by many different cells including COS-7 cells (Yanagita et al., "Processing of mutated proinsulin with tetrabasic cleavage sites to mature insulin reflects the expression of furin in nonendocrine cell lines," *Endocrinology* 133: 639-644 (1993)), PK2L is probably cleaved by endogenous furin during secreting from COS-7 cells. Indeed, co-expression of furin facilitates the cleavage process.

Since PK2β is the mature form of PK2L, the study described herein focused on PK2β. The pharmacological properties of PK2β were compared to those of PK1 and PK2. The results indicate that while both PK1 and PK2 potently activate $Ca^{2+}$ mobilization in both PKR1 and PKR2 expressing cells, PK2β much more potently stimulates PKR1 than PKR2. PK2β was also tested in comparison with PK1 and PK2 in radioligand binding assays. From an attempt to label PK1 using $^{125}I$ at $Tyr^{75}$ in human PK1 as the radioligand, the resulting radioligand produced very little specific binding in the binding assays using either PKR1 or PKR2 expressing cells. Since PK2 does not have a Tyr, the C-terminal FLAG-tagged PK2, which has a Tyr in the FLAG-tag, was expressed and labeled with $^{125}I$. The $^{125}I$-PK2-FLAG binds PKR1 and PKR2 with high affinities and produces average signal to noise ratio of 8:1 in the binding assays. $^{125}I$-PK2-FLAG was therefore used as the tracer in the competition assays to characterize unlabeled PK1, PK2, and PK2β. The binding results show that PK2β preferentially binds PKR1 over PKR2, which agrees with our $Ca^{2+}$ mobilization experiments. PK2 showed much greater affinity for both PKR1 and PKR2 in the binding assays than either PK1 or PK2β. PK1 showed high potency in $Ca^{2+}$ assays but much lower potency in the binding assays. The decreased potency of PK1 in the binding assays may explain the reduced binding observed when using $^{125}I$-PK1 as the radioligand. The difference of $EC_{50}$ and $IC_{50}$ values could be a result of the differences in the assay mechanisms.

The 56-amino acid sequence of the PK2β mature peptide (SEQ ID NO.: 1) possesses only 47 amino acids of the N-terminus of PK2 and still acts as a potent full agonist for PKR1, indicating that the functional domain of PK is located at the N-terminus. Indeed, sequence comparisons among PK1, PK2, MIT, and BV8 indicate that they share much higher conservations at the N-terminus than at the C-terminus.

Some G-protein coupled receptors have been shown to interact with different G-proteins, including $G_q$, $G_i$ and $G_s$ proteins (Chabre et al., "Coupling of the alpha 2A-adrenergic receptor to multiple G-proteins. A simple approach for estimating receptor-G-protein coupling efficiency in a transient expression system," *J Biol Chem* 269:5730-5734 (1994); Liu et al., "Involvement of both Gq/11 and $G_s$ proteins in gonadotropin-releasing hormone receptor-mediated signaling in LβT2 cells," *J Biol Chem* 277:32099-32108 (2002); Lin et. al., 2002a, supra; Sago et. al., 2002, supra), and therefore PKRs appear to be coupled with $G_q$ proteins. The fact that PK-induced activation of MAPK is PTX-sensitive (Lin et al., 2002b, supra) indicates that PKR may be also coupled with $G_i$ proteins. Indeed, our results show that the co-expression of $G_{qi5}$ with PKR2 increases PK-stimulated $Ca^{2+}$ response in PKR2-expressing cells.

The results from an investigation into whether PK stimulates cAMP in PKR-expressing cells indicate that PK1, PK2, and PK2β stimulated cAMP accumulation in PKR expression cells in a dose-dependent manner. Consistent results were obtained when performing the cAMP accumulation assays in either stable SK-N-MC cells or HEK293 cells transiently expressing PKR1 and PKR2. Co-expression of $G_s$ protein with PKRs enhanced the PK stimulated cAMP accumulation, reflecting that PKR can couple with $G_s$ proteins.

Since the PK receptors can couple to different signal transduction pathways through different classes of G-proteins, natural cells expressing PKR but with different G-protein expression patterns may respond to PK differently, thus allowing those cells to perform different physiological functions.

PK2β acts as an agonist for PKR1 and is therefore useful for treating diseases or disorders mediated by PKR1 activity. The peptidic compounds of the invention may be administered in conventional formulations for peptides, such as those described in the latest edition of *Remington's Pharmaceutical*

Sciences, Mack Publishing Company (Easton, Pa.). Preferably, a peptide is administered by injection, preferably intravenously, using a suitable formulation for this route of administration. Alternatively, the peptide may be administered by constant infusion over an extended period of time until the desired therapeutic benefit is obtained. Other modes of administration include, e.g., suppositories, intranasal aerosols, and, where appropriate, oral formulations.

Compositions of the invention preferably contain an effective amount of the PK2β peptide—i.e., an amount effective to achieve the desired therapeutic effect through PKR1 modulation. Exemplary dosage levels are about from 0.001 to 1000 µg/kg subject, more preferably 0.001 to 100 µg/kg, with the selection of an appropriate dosage being within the purview of the ordinarily skilled artisan.

Thus, the invention also provides pharmaceutical compositions comprising an effective amount of the inventive peptides or nontoxic addition salts, amides, or esters thereof. Pharmaceutically acceptable, nontoxic salts include, e.g., acid addition salts formed with the free amino groups using inorganic acids, such as hydrochloric or phosphoric acids, or organic acids, such as acetic, oxalic, tartaric, mandelic acids and the like. Salts formed with the free carboxyl groups may be derived from inorganic bases, such as sodium, potassium, ammonium, calcium, or ferric hydroxides, and organic bases, such as isopropylamine, trimethylamine, 2-ethylamino ethanol, histidine, procaine, and the like.

Preferably, the compositions comprise in addition to the peptidic compound one or more physiologically tolerable or pharmaceutically acceptable liquid, gel, or solid diluents, adjuvants, excipients, vehicles, and/or carriers. Suitable diluents and excipients include, e.g., water, saline, dextrose, glycerol, and the like, and combinations thereof. Additionally, if desired the compositions may further contain minor amounts of auxiliary ingredients, such as wetting or emulsifying agents, stabilizing or pH-buffering agents, and the like. Optionally, the compositions may contain other active ingredients or may be co-administered with another pharmaceutical composition.

Peptides of the invention may also be used for preparing antisera for use in immunoassays employing labeled reagents, e.g., antibodies. The peptidic compounds may be conjugated to an antigenicity-conferring carrier, as appropriate, by means of dialdehydes, carbodiimide, or using commercially available linkers. The compounds and immunologic reagents may be labeled with various labels, e.g., chromophores, fluorophores (such as fluorescein or rhodamine), radioisotopes (such as $^{125}$I, $^{5}$S, $^{14}$C, or $^{3}$H) or magnetized particles using means known in the art. These labeled compounds and reagents, or labeled reagents capable of recognizing and specifically binding to them, may find use as diagnostic reagents. Samples derived from biological specimens may be assayed for presence or amount of substances having a common antigenic determinant with compounds of the invention. Additionally, monoclonal antibodies may be prepared using known techniques, which antibodies may have therapeutic use, e.g., to neutralize overproduction of immunologically related compounds in vivo.

Although the invention has been described by reference to a detailed description and its preferred embodiments, it will be understood that the scope of the invention is defined not by the foregoing description, but by the appended claims as properly construed under principles of patent law.

What is claimed is:

1. An isolated and purified peptide consisting of an amino acid sequence selected from the group consisting of AVITGACDKDSQCGGGMCCAVSIWVKSIRICTPMGKLGDSCHPLTRKNNFGNGRQE (SEQ.ID.NO.:1) and AVITGACDKDSQCGGGMCCAVSIWVKSIRICTPMGQVGDSCHPLTRKSHVANGRQE (SEQ.ID.NO.:2), or a salt, amide, or ester thereof.

2. An isolated and purified PK2β peptide having the amino acid sequence of SEQ.ID.NO.:1.

3. An isolated and purified PK2β peptide having the amino acid sequence of SEQ.ID.NO.:2.

* * * * *